United States Patent [19]

Rowland et al.

[11] Patent Number: 5,488,052

[45] Date of Patent: Jan. 30, 1996

[54] AQUEOUS FLOWABLE FENAZAQUIN COMPOSITION COMPRISING SODIUM NAPHTHALENE FORMALDEHYDE CONDENSATES

[75] Inventors: Larry B. Rowland, New Palestine; Joseph R. Winkle, Cumberland, both of Ind.

[73] Assignee: DowElanco, Indianapolis, Ind.

[21] Appl. No.: 410,553

[22] Filed: Mar. 24, 1995

Related U.S. Application Data

[63] Continuation of Ser. No. 890,500, May 28, 1992.

[51] Int. Cl.$^6$ .......................... A01N 43/54; A01N 43/78; A01N 25/22; A01N 25/30
[52] U.S. Cl. ..................... 514/259; 514/772; 514/971
[58] Field of Search ................................ 514/259, 772, 514/971

[56] References Cited

U.S. PATENT DOCUMENTS

| | | | |
|---|---|---|---|
| 3,948,636 | 4/1976 | Marks | 71/112 |
| 4,071,617 | 1/1978 | Graves et al. | 424/78 |
| 4,197,112 | 4/1980 | Albert et al. | 71/DIG. 1 |
| 4,367,104 | 1/1983 | Paton et al. | 149/7 |
| 5,139,773 | 8/1992 | Tadros | 514/315 |

FOREIGN PATENT DOCUMENTS 0326329  8/1989  European Pat. Off. .

OTHER PUBLICATIONS

*Farm Chemicals Handbook* '87, "Flowable Formulation". p. C118. 1987.

Primary Examiner—S. Mark Clardy
Attorney, Agent, or Firm—Dugal S. Sickert

[57] ABSTRACT

The present invention relates to a novel aqueous flowable composition of fenazaquin. It was found that conventional aqueous flowable formulations resulted in a product that lost miticidal activity during storage. The low miticidal activity was found to be due to an unacceptable level of particle size growth during storage. It has been found that an aqueous flowable fenazaquin formulation of satisfactory particle size stability can be made when a higher than normal concentration of sodium naphthalene formaldehyde condensate dispersant is utilized in the formulation.

6 Claims, No Drawings

# AQUEOUS FLOWABLE FENAZAQUIN COMPOSITION COMPRISING SODIUM NAPHTHALENE FORMALDEHYDE CONDENSATES

This is a continuation of application Ser. No. 07/890,500 filed May 28, 1992, now abandoned.

BACKGROUND OF THE INVENTION

The present invention relates to an aqueous flowable composition for fenazaquin. Fenazaquin is the generic name for 4-[2-[4-(t-butyl)-phenyl]ethoxy]-quinazoline. It is representative of a new and useful class of miticidal compounds disclosed in EPO Application 89300657.7, filed Jan. 25, 1989.

An aqueous flowable composition, or simply, an aqueous flowable, is one type of agricultural formulation. An aqueous flowable is a formulation typically comprising an active ingredient which is a finely ground water-insoluble solid displaying good storage stability and is stable in the dispersing medium. The formulation will also typically include some or all of the following: a surfactant, suspending agent, anticaking or flow aid, dispersant, defoamer, and freeze-point depressant, all of which are selected so that the formulation can be readily mixed in a liquid dispersing medium, such as water, or an anhydrous organic solvent such as mineral oil, fatty oils, or glycol ethers, to form a stable suspension suitable for spray application. These formulations are made by standard techniques, well known in the art.

The surfactant acts as a wetting agent to reduce the surface tension at the water-solid interface, and therefore increases the tendency of the water to contact the complete surface of the active ingredient particles. Both anionic and/or nonionic surfactants may play a role in the stabilization of a flowable formulation. For a water-based flowable, the surfactant must be water soluble, at least to the concentration limit desired for the lower temperature limit. Examples of surfactants include anionic surfactants such as alkyl polyether alcohol sulfates, arylalkyl polyether alcohol sulfates, arylalkyl sulfonates, alkylnapthalene sulfonates, and alkyl phenoxybenzene disulfonates, and nonionic surfactants, such as arylalkyl polyether alcohols, alkyl polyether alcohols, polyoxyethylene fatty acid esters, polyethylene sorbitan fatty acid esters, polyalkylene oxide block copolymers, polyalkylene oxide block copolymer monohydric alcohols, and polyalkylene oxide block copolymer alkyl phenols. Aqueous flowables typically contain 0.5–10% by weight of a surfactant.

The suspending agent acts as a thickening agent or thixotrope in maintaining the dispersed, micron sized particles of the formulation in suspension. The suspending agent is a water soluble or water dispersible anionic colloid possessing shear thinning properties, low sensitivity to temperature, good stability in both acidic and basic media, and is compatible with most inorganic materials. Examples of suspending agents include xanthan gums, organically modified montmorillonite clays, attapulgite clays, carboxy-vinyl copolymers, and cellulose ethers. Aqueous flowables typically contain 0.02–1% by weight of a suspending agent.

An anticaking agent or flow aid is a diluent which may be necessary to help improve the resuspensibility of the diluted spray, reduce the ultimate particle size of the active ingredient by acting as a grinding aid or lubricant in the milling process, modify the surface of the active ingredient thus inhibiting its crystal growth potential, and perform as a viscosity-modifying agent. Examples of anticaking agents or flow aids include kaolinite clays, diatomites, synthetic silicas, and attapulgites. Aqueous flowables typically contain 0–10% by weight of an anticaking agent or flow aid.

The dispersing agent is a polar organic material with surface active properties that orients itself between particles of active ingredient, and by virtue of size or charge, reduces the cohesiveness or attraction of the active ingredient particles for each other. In addition to imparting this physical stability to the aqueous mixture, dispersants may also aid in the redispersibility of the diluted spray mixture. The dispersing agent must be carefully selected and used to avoid problems such as foaming. Examples of dispersants include the salts of the lignosulfonic acids, the polymerized alkyl, arylalkyl or naphthalene sulfonic salts, and high molecular weight anionic surfactants. Aqueous flowables typically contain 0.1–2% by weight of a dispersing agent.

An antifoam agent, or defoamer, may be needed in the formulation if the surfactant or dispersant selected produces a stable foam when diluted with water. An antifoam agent may also be needed as a processing aid in milling to prevent aeration in the grinding stock dispersion because stable foamation during the milling process decreases the intimate contact between the grinding media and the active ingredient, thus decreasing grinding efficiency. Example of defoamers include the dimethylpolysiloxanes, ANTIFOAM A, ANTIFOAM C, ANTIFOAM FG-10, ANTIFOAM DB-100, AND ANTIFOAM AF-100 (Dow Corning). Aqueous flowables typically contain 0–1.0% by weight of a defoamer.

A freeze-point depressant may be necessary to ensure good low temperature stability. The more common examples of freeze-point depressants include ethylene and propylene glycol. However, sorbitol and glycerol may also be typically used. Functionally, in addition to lowering the freezing point of the water solvent, the freeze-point depressant may aid in preventing drying and skinning by acting as a humectant, controlling viscosity, removing hydrophobic impurities, and assisting the wetting process before and during milling. Aqueous flowables typically contain 2–10% by weight of a freeze-point depressant.

An antimicrobial agent may be necessary to prevent growth of bacteria, fungi, or other microbial organisms that can flourish in an aqueous environment. Also, the presence of xanthan gums, found in many aqueous flowable formulations, can accelerate the organism growth since the gums can act as a food source for the microbial organism. An example of an antimicrobial agent is PROXEL GXL (1,2-benzisothiazolin-3-one, ICI). Aqueous flowables typically contain 0–0.2% of an antimicrobial agent.

To facilitate handling and use, agrochemicals are not typically sold in the form of pure active ingredient or technical material, but instead, are typically sold as a formulated composition product. If the material is to be applied by spraying, it may typically be applied as an aqueous flowable. In such case, the product obtained by the applicator is a formulated product that can be readily mixed with water to form an aqueous flowable product. The product may then be applied from all types of presently used spray equipment.

Efforts to formulate fenazaquin as a conventional aqueous flowable formulation resulted in compositions of low miticidal activity. It was found that conventional aqueous flowable formulations resulted in a product that lost miticidal activity during storage. The low miticidal activity was found to be due to an unacceptable level of particle size growth during storage. Conventional aqueous flowable fenazaquin formulations were found to increase in particle size, apparently by crystal growth or Ostwald ripening, agglomeration, or by both. The size of the particles is important as the miticidal efficacy of an aqueous flowable fenazaquin product depends upon the average particle size remaining less than seven microns, or preferably, less than four microns.

DESCRIPTION OF THE INVENTION

Initial studies with early aqueous flowable formulations of fenazaquin showed the propensity of fenazaquin to grow in particle size in an aqueous environment. The solubility of fenazaquin in various formulation ingredients was determined based upon a classical Ostwald ripening effect. Fenazaquin was found to have little or no solubility (<500 ppm) at 52° C. in glycerin, lignosulfonate dispersants, silicone based wetting agents, ethylene oxide propylene oxide low molecular weight block copolymers, and other specific surfactants and dispersants. These aqueous flowable formulations of fenazaquin, which should have shown no potential for crystal growth based on solubility, were evaluated. However, crystal growth was observed.

Since dispersants at normal levels earlier showed no effect on slowing down crystal growth, a series of dispersants were utilized at excessive levels compared to normal use. Quite surprisingly, one dispersant in particular, MORWET D-425 (sodium naphthalene formaldehyde condensate, DeSoto, Inc.),gave excellent results in slowing crystal growth to an acceptable level.

Accordingly, applicants have discovered an aqueous flowable composition of fenazaquin that prevents the growth of fenazaquin particles to an average size greater than seven microns. It has been unexpectedly found that a satisfactory aqueous flowable fenazaquin formulation can be made when a higher than normal concentration of dispersant is utilized in the formulation.

This formulation may generally contain, by weight, (a) 10%–20% fenazaquin, (b) 0.5%–10% one or more surfactants, (c) 0.02%–1.0% one or more suspending agents, (d) 0%–10% one or more anticaking or flow aids, (e) 5%–15% one or more dispersants, (f) 0.1%–1.0% one or more defoaming agents, (g) 2%–10% one or more freeze-point depressants, (h) 0.02–0.2% one or more antimicrobial agents, and (i) 50%–85% water.

A preferred formulation may generally contain, by weight, (a) 15%–20% fenazaquin, (b) 0.5%–2% one or more surfactants, (c) 0.6%–1.0% one or more suspending agents, (d) 6%–12% one or more dispersants, (e) 0.1%–0.5% one or more defoaming agents, (f) 4%–8% one or more freeze-point depressants, (g) 0.02–0.2% one or more antimicrobial agents, and (h) 60%–80% water.

Preferred surfactants include MORWET EFW (sulfated alkyl carboxylate and sulfonated alkyl naphthalene sodium salt, DeSoto, Inc.), PLURONIC P-103 (ethylene oxide propylene oxide block copolymer, BASF), and SILWET L-77 (polyethoxysilane surfactant, Union Carbide).

A preferred dispersant is MORWET D-425.

EXAMPLES

The following nonlimiting examples are provided to illustrate the invention described herein.

Example 1

An aqueous flowable composition was prepared according to the following formulation and method:

| Ingredient | % weight/weight |
|---|---|
| Fenazaquin | 18.76 |
| MORWET EFW | 1.00 |
| MORWET D-425 | 12.00 |
| ANTIFOAM AF-100 | 0.40 |
| PROXEL GXL (antimicrobial agent, ICI) | 0.05 |
| VEEGUM ($SiO_2$ based, R.T. Vanderbilt) | 0.60 |
| KELZAN (xanthan gum, Kelco) | 0.15 |
| propylene glycol | 8.00 |
| water | 59.04 |

Grind. In a stainless steel beaker was combined 1775 gm water, 100 gm MORWET EFW, 200 gm MORWET D-425, and 20 gm ANTIFOAM AF-100, with stirring until uniform. About one-half of this slurry was added to a Q 1.5 attritor and stirred for two to three minutes. To the attritor was added 938 gm of fenazaquin and grinding continued for one hour. Several times during the grind, about one pint from the bottom of the slurry was taken and added back to the top. After one hour the grind was stopped and the grind solution was drained. The remaining one-half of the slurry was added to the grind solution and the mixture was stirred for two to three minutes. The remaining 938 gm of fenazaquin was added to this mixture and the mixture and grinding was commenced for one hour.

Suspending slurry. In a stainless steel beaker was combined 1700 gm of water, 5 gm of PROXEL GXL, and 60 gm of VEEGUM with stirring for about two to three minutes. In a separate beaker was combined 800 gm of propylene glycol and 15 gm KELZAN with stirring. This mixture was then slowly added to the above mixture of water, PROXEL, and VEEGUM, and sheared with a dispersator for about 45 minutes.

Dispersant slurry. In a four liter stainless steel beaker was combined 1000 gm of water and 20 gm of ANTIFOAM AF-100. To this mixture was slowly added 1000 gm of MORWET D-425 with stirring for about 30 minutes.

Recovery. After the second one hour grind, the attritor was drained. To the attritor was added about one-half of the dispersant slurry with stirring for two to three minutes. The attritor was again drained. The remaining dispersant slurry was added to the attritor with stirring for two to three minutes and the attritor was again drained. To the attritor was added 1429 gm of water with stirring for two to three minutes. The attritor was again drained and a total of 7245 gm of grind rinse solution was recovered. To the recovered solution was added 2519.1 gm of the suspending aid solution with stirring for about 30 minutes.

Particle analysis. A Coulter Counter, Model TAII, which determines the number and size distribution of particles suspended in an electrolyte solution by measuring the change in conductivity as particles pass through a small aperture in the counter device, was utilized as follows:

A 5–10% mixture of the fenazaquin was prepared in the electrolyte solution, ISOTON II (Coulter), and then sonicated two to three minutes to assure complete dispersion of the particles. A sample of this mixture was then diluted further in the electrolyte solution to about a 3% concentration. This mixture was continuously stirred by the Coulter Counter device. A stopcock located on the aperture tube of the device was then opened producing a vacuum inside the tube. The reset button was then depressed which cleared the counter and applied current to the electrodes. With the readout switch in the total count position, the accumulate button was depressed and the count of the particles began and continued until the count reached 100,000–150,000. Then, the stop button was depressed and the stopcock closed.

To obtain the cumulative results, a sheet of Coulter graph paper was placed on the plotter, the readout switch was set to the % volume position, the scope display switch was set to cumulative plot, and the plot button was depressed. To obtain the differential results, the display switch was set to differential plot and the plot button was again depressed. The median particle size was obtained from the cumulative plot by measuring the particle size in microns at the 50% level.

Results. Particle size analysis was conducted by the above method on samples of the above composition taken over a 15 week period at 37° C., room temperature (R.T.), and 52° C. The results obtained, in microns ($\mu$), were as follows:

| Time | 37° C. | R.T. | 52° C. |
| --- | --- | --- | --- |
| Initial | –* | 1.9 | – |
| 2 weeks | – | 1.9 | 2.3 |
| 23 days | 1.9 | 1.95 | 2.6 |
| 5 weeks | 1.9 | 1.95 | 2.7 |
| 7.5 weeks | 1.9 | 1.95 | 3.0 |
| 8 weeks | 1.9 | 1.95 | – |
| 12 weeks | 1.9 | 1.95 | 3.1 |
| 15 weeks | 1.95 | 1.9 | – |

(*"–" indicates no measurement was taken).

Example 2

According to the general procedure disclosed in Example 1, above, an aqueous flowable composition was prepared according to the following formulation:

| Ingredient | % weight/weight |
| --- | --- |
| Fenazaquin | 11.90 |
| PLURONIC P-103 | 1.50 |
| PROXEL GXL | 0.05 |
| ANTIFOAM AF-100 | 0.20 |
| REAX 88B | 1.00 |
| (lignosulfonate, Westvaco) | |
| VEEGUM | 0.75 |
| xanthan gum | 0.25 |
| ZEOSYL 200 | 0.50 |
| (silicate, Huber) | |
| water | 83.85 |

Particle analysis and results. Particle size analysis was conducted by the general method disclosed in Example 1, above, on samples of the above composition taken over a 3 week period at room temperature (R.T.) and 52° C. The results obtained, in microns ($\mu$), were as follows:

| Time | R.T. | 52° C. |
| --- | --- | --- |
| Initial | 1.2 | 1.2 |
| 1 week | 1.5 | 4.0 |
| 3 weeks | – | large crystals which blocked aperture |

Example 3

According to the general procedure disclosed in Example 1, above, an aqueous flowable composition was prepared according to the following formulation:

| Ingredient | % weight/weight |
| --- | --- |
| Fenazaquin | 11.90 |
| PLURONIC P-103 | 1.50 |
| PROXEL GXL | 0.05 |
| ANTIFOAM AF-100 | 0.20 |
| REAX 88B | 1.00 |
| VEEGUM | 0.75 |
| xanthan gum | 0.25 |
| water | 84.35 |

Particle analysis and results. Particle size analysis was conducted by the general method disclosed in Example 1, above, on samples of the above composition taken over a 4 week period at room temperature (R.T.) and 52° C. The results obtained, in microns ($\mu$), were as follows:

| Time | R.T. | 52° C. |
| --- | --- | --- |
| Initial | 1.2 | 1.2 |
| 1 week | 1.4 | 3.4 |
| 4 weeks | – | 5.4 |

Example 4

According to the general procedure disclosed in Example 1, above, an aqueous flowable composition was prepared according to the following formulation:

| Ingredient | % weight/weight |
| --- | --- |
| Fenazaquin | 11.90 |
| PLURONIC P-103 | 1.50 |
| PROXEL GXL | 0.05 |
| ANTIFOAM AF-100 | 0.20 |
| REAX 88B | 1.00 |
| VEEGUM | 0.75 |
| xanthan gum | 0.25 |
| Barden clay | 0.50 |
| water | 83.85 |

Particle analysis and results. Particle size analysis was conducted by the general method disclosed in Example 1, above, on samples of the above composition taken over a 3 week period at room temperature (R.T.) and 52° C. The results obtained, in microns ($\mu$), were as follows:

| Time | R.T. | 52° C. |
| --- | --- | --- |
| Initial | 1.4 | 1.2 |
| 1 week | 1.7 | 4.0 |
| 3 weeks | 1.8 | large crystals which blocked |

EXAMPLE 5

According to the general procedure disclosed in Example 1, above, an aqueous flowable composition was prepared according to the following formulation:

| Ingredient | % weight/weight |
| --- | --- |
| Fenazaquin | 11.90 |
| ICONOL OP10 | 1.50 |
| (octylphenyl ethoxylate, DeSoto) | |
| PROXEL GXL | 0.05 |
| ANTIFOAM AF-100 | 0.20 |
| MORWET D-425 | 1.00 |
| VEEGUM | 0.75 |
| xanthan gum | 0.25 |
| Barden clay | 0.50 |
| water | 83.85 |

Particle analysis and results. Particle size analysis was conducted by the general method disclosed in Example 1, above, on samples of the above composition taken over a 3 week period at room temperature (R.T.) and 52° C. The results obtained, in microns (μ), were as follows:

| Time | R.T. | 52° C. |
| --- | --- | --- |
| Initial | 1.3 | 1.3 |
| 1 week | 1.6 | 4.7 |
| 3 weeks | 2.0 | 12.5 |

Example 6

According to the general procedure disclosed in Example 1, above, an aqueous flowable composition was prepared according to the following formulation:

| Ingredient | % weight/weight |
| --- | --- |
| Fenazaquin | 12.20 |
| PLURONIC P-103 | 1.50 |
| PROXEL GXL | 0.05 |
| ANTIFOAM AF-100 | 0.20 |
| REAX 88B | 1.00 |
| glycerin | 4.00 |
| VEEGUM | 0.75 |
| KELZAN | 0.25 |
| water | 80.05 |

Particle analysis and results. Particle size analysis was conducted by the general method disclosed in Example 1, above, on samples of the above composition taken over a 1 month period at room temperature (R.T.) and 52° C. The results obtained, in microns (μ), were as follows:

| Time | R.T. | 37° C. | 52° C. |
| --- | --- | --- | --- |
| Initial | 2.7 | – | – |
| 1 week | 2.7 | 3.5 | 4.3 |
| 1 month | 2.8 | 3.7 | 5.0 |

Example 7

According to the general procedure disclosed in Example 1, above, an aqueous flowable composition was prepared according to the following formulation:

| Ingredient | % weight/weight |
| --- | --- |
| Fenazaquin | 12.20 |
| MORWET EFW | 0.75 |
| LOMAR PWM | 7.00 |
| (alkyl naphthalene sulfonate | |
| condensates, Henkel) | |
| PROXEL GXL | 0.05 |
| ANTIFOAM AF-100 | 0.20 |
| glycerin | 4.00 |
| VEEGUM | 0.75 |
| KELZAN | 0.25 |
| water | 74.80 |

Particle analysis and results. Particle size analysis was conducted by the general method disclosed in Example 1, above, on samples of the above composition taken over a 1 month period at room temperature (R.T.) and 52° C. The results obtained, in microns (μ), were as follows:

| Time | R.T. | 52° C. |
| --- | --- | --- |
| Initial | 2.0 | – |
| 1 week | – | 6.3 |
| 1 month | – | – |

Example 8

According to the general procedure disclosed in Example 1, above, an aqueous flowable composition was prepared according to the following formulation:

| Ingredient | % weight/weight |
| --- | --- |
| Fenazaquin | 12.20 |
| MORWET EFW | 0.75 |
| DISPERSOGEN A | 7.00 |
| (alkyl naphthalene sulfonate | |
| condensates, Hoechst) | |
| PROXEL GXL | 0.05 |
| ANTIFOAM AF-100 | 0.20 |
| glycerin | 4.00 |
| VEEGUM | 0.75 |
| KELZAN | 0.25 |
| water | 74.80 |

Particle analysis and results. Particle size analysis was conducted by the general method disclosed in Example 1, above, on samples of the above composition taken over a 1 month period at room temperature (R.T.) and 52° C. The results obtained, in microns (μ), were as follows:

| Time | R.T. | 52° C. |
| --- | --- | --- |
| Initial | 4.2 | – |
| 1 week | – | 11.0 |
| 1 month | – | – |

Example 9

According to the general procedure disclosed in Example 1, above, an aqueous flowable composition was prepared according to the following formulation:

| Ingredient | % weight/weight |
|---|---|
| Fenazaquin | 12.20 |
| MORWET EFW | 0.75 |
| REAX 88B | 7.00 |
| PROXEL GXL | 0.05 |
| ANTIFOAM AF-100 | 0.20 |
| glycerin | 4.00 |
| VEEGUM | 0.75 |
| KELZAN | 0.25 |
| water | 74.80 |

Particle and results. Particle size analysis was conducted by the general method disclosed in Example 1, above, on samples of the above composition taken over a 1 month period at room temperature (R.T.) and 52° C. The results obtained, in microns (μ), were as follows:

| Time | R.T. | 52° C. |
|---|---|---|
| Initial | 2.65 | – |
| 1 week | – | 7.5 |
| 1 month | – | – |

Example 10

According to the general procedure disclosed in Example 1, above, an aqueous flowable composition was prepared according to the following formulation:

| Ingredient | % weight/weight |
|---|---|
| Fenazaquin | 12.20 |
| MORWET EFW | 0.75 |
| POLYFON H (lignosulfonic acid, Westvaco) | 7.00 |
| PROXEL GXL | 0.05 |
| ANTIFOAM AF-100 | 0.20 |
| glycerin | 4.00 |
| VEEGUM | 0.75 |
| KELZAN | 0.25 |
| water | 74.80 |

Particle analysis and results. Particle size analysis was conducted by the general method disclosed in Example 1, above, on samples of the above composition taken over a 1 month period at room temperature (R.T.) and 52° C. The results obtained, in microns (μ), were as follows:

| Time | R.T. | 52° C. |
|---|---|---|
| Initial | 2.8 | – |
| 1 week | – | 7.4 |
| 1 month | – | – |

Example 11

According to the general procedure disclosed in Example 1, above, an aqueous flowable composition was prepared according to the following formulation:

| Ingredient | % weight/weight |
|---|---|
| Fenazaquin | 12.20 |
| MORWET EFW | 0.75 |
| Crystal Growth Inhibitor #5, (Harcross) | 7.00 |
| PROXEL GXL | 0.05 |
| ANTIFOAM AF-100 | 0.20 |
| glycerin | 4.00 |
| VEEGUM | 0.75 |
| KELZAN | 0.25 |
| water | 74.80 |

Particle analysis and results. Particle size analysis was conducted by the general method disclosed in Example 1, above, on samples of the above composition taken over a 1 month period at room temperature (R.T.) and 52° C. The results obtained, in microns (μ), were as follows:

| Time | R.T. | 52° C. |
|---|---|---|
| Initial | 5.6 | – |
| 1 week | – | 9.0 |
| 1 month | – | – |

Example 12

According to the general procedure disclosed in Example 1, above, an aqueous flowable composition was prepared according to the following formulation:

| Ingredient | % weight/weight |
|---|---|
| Fenazaquin | 12.20 |
| MORWET EFW | 0.75 |
| MORWET D-425 | 7.00 |
| PROXEL GXL | 0.05 |
| ANTIFOAM AF-100 | 0.20 |
| glycerin | 4.00 |
| VEEGUM | 0.75 |
| KELZAN | 0.25 |
| water | 74.80 |

Particle analysis and results. Particle size analysis was conducted by the general method disclosed in Example 1, above, on samples of the above composition taken over a 1 month period at room temperature (R.T.) and 52° C. The results obtained, in microns (μ), were as follows:

| Time | R.T. | 52° C. |
|---|---|---|
| Initial | 2.1 | – |
| 1 week | – | 2.5 |
| 1 month | – | 2.6 |

Example 13

According to the general procedure disclosed in Example 1, above, an aqueous flowable composition was prepared according to the following formulation:

| Ingredient | % weight/weight |
|---|---|
| Fenazaquin | 12.20 |
| MORWET EFW | 0.75 |
| MORWET D-425 | 6.00 |
| PROXEL GXL | 0.05 |
| ANTIFOAM AF-100 | 0.20 |
| glycerin | 4.00 |
| VEEGUM | 0.75 |
| KELZAN | 0.25 |

-continued

| Ingredient | % weight/weight |
|---|---|
| water | 75.80 |

Particle analysis and results. Particle size analysis was conducted by the general method disclosed in Example 1, above, on samples of the above composition taken over a 6 week period at room temperature (R.T.) and 52° C. The results obtained, in microns (μ) follows:

| Time | R.T. | 52° C. |
|---|---|---|
| Initial | 1.25 | – |
| 2 day | 1.25 | 1.5 |
| 4 day | – | 1.5 |
| 1 week | – | 1.6 |
| 2 week | – | 1.9 |
| 4 week | – | 1.95 |
| 6 week | – | 2.0 |

Example 14

According to the general procedure disclosed in Example 1, above, an aqueous flowable composition was prepared according to the following formulation:

| Ingredient | % weight/weight |
|---|---|
| Fenazaquin | 12.20 |
| MORWET EFW | 0.75 |
| MORWET D-425 | 5.00 |
| PROXEL GXL | 0.05 |
| ANTIFOAM AF-100 | 0.20 |
| glycerin | 4.00 |
| VEEGUM | 0.75 |
| KELZAN | 0.25 |
| water | 76.80 |

Particle analysis and results. Particle size analysis was conducted by the general method disclosed in Example 1, above, on samples of the above composition taken over a 1 week period at room temperature (R.T.) and 52° C. The results obtained, in microns (μ), were as follows:

| Time | R.T. | 52° C. |
|---|---|---|
| 2 day | 1.25 | 1.9 |
| 4 day | – | 2.2 |
| 1 week | – | 2.2 |

Example 15

Bioassay Method. Bioassays may be conducted on a variety of plant surfaces. These consist of bountiful bushbean, squash cotyledons, apple, cotton, and orange. Small seedlings are used and are trimmed to two leaves. The leaves of bushbean are further trimmed to reduce the total surface area to one square inch in order to provide similar areas for each surface and to facilitate observation accuracy. Acute activity is determined by preinfesting each leaf 24 hours prior to treatment with 50 to 100 of a mixed population of twospotted spider mites (*Tetranychus urticae*). Plants are sprayed to wetting with the desired concentration and formulation using a Devilbiss atomizer. Treatments are replicated four times and randomly distributed in a greenhouse for holding. Mortality readings are taken 24 hours posttreatment by estimating the percent of morbid mites on each leaf through a dissecting microscope. Residual activity is determined using the above procedure but infesting the seedling 24 hours posttreatment. Ovicidal activity of the different formulations are compared by preinfesting squash cotyledons with a mixed population containing 50 to 100 adult female twospotted spider mites. Twenty-four hours after infestation, all mobile forms are removed by immersing the leaves for 90 seconds in 90% ethanol. Plants are then rinsed with water and allowed to dry. Data is analyzed using probit analysis.

Results. Acute activity analysis was conducted by the above general method on samples of an aqueous flowable fenazaquin composition prepared according to Example 1. Rate is the concentration of active ingredient on a weight/weight basis in the spray solution expressed in parts per million (ppm). Mortality is the percent of morbid mites determined by the above methods. The results obtained were as follows:

| Rate (ppm) | Acute Mortality |
|---|---|
| 0.00 | 0.00 |
| 1.00 | 2.50 |
| 5.00 | 71.25 |
| 10.00 | 95.75 |
| 20.00 | 97.25 |
| 50.00 | 99.75 |
| 100.00 | 99.75 |
| 200.00 | 100.00 |

Example 16

Samples of varying particle size and concentration of an aqueous flowable fenazaquin composition prepared according to Example 6 were analyzed according to the general bioassay method of Example 15. The results obtained were as follows:

| Size (μ) | Rate (ppm) | Acute Mortality | Residual Mortality | Ovicidal Mortality |
|---|---|---|---|---|
| 2.3 | 5 | 50 | 65 | 95 |
| 2.3 | 10 | 100 | 99 | 100 |
| 2.3 | 50 | 100 | 100 | 100 |
| 3.7 | 5 | 50 | 60 | 93 |
| 3.7 | 10 | 100 | 100 | 100 |
| 3.7 | 50 | 100 | 100 | 100 |
| 6.0 | 5 | 50 | 40 | 53 |
| 6.0 | 10 | 99 | 98 | 92 |
| 6.0 | 50 | 100 | 100 | 100 |
| 9.5 | 5 | 87 | 0 | 8 |
| 9.5 | 10 | 100 | 23 | 79 |
| 9.5 | 50 | 100 | 100 | 100 |
| 11.3 | 5 | 30 | 0 | 4 |
| 11.3 | 10 | 60 | 8 | 73 |
| 11.3 | 50 | 99 | 100 | 100 |
| 15.0 | 5 | 0 | 0 | 0 |
| 15.0 | 10 | 0 | 0 | 0 |
| 15.0 | 50 | 85 | 100 | 100 |

We claim:

1. An aqueous flowable composition comprising by % weight:
   (a) 15%–20% fenazaquin,
   (b) 0.5%–2% one or more surfactants,
   (c) 0.02%–1.0% one or more suspending agents,
   (d) 0–10% one or more anticaking or flow aids,
   (e) 6%–12% one or more dispersants which are sodium napthalene formaldehyde condensates, (f) 0–0.5% one or more defoamers, (g) 4%–8% one or more freeze point depressants, (h) 0–0.2% one or more antimicrobial agents, and (i) 50%–80% water.

2. A composition of claim 1 wherein the surfactants are sulfated alkyl carboxylate and sulfonated alkyl napthalene sodium salts, ethylene oxide propylene oxide block copolymers, and polyethoxysilane surfactants.

3. A composition of claim 2 wherein the surfactant is a sulfated alkyl carboxylate and sulfonated alkyl napthalene sodium salt.

4. An aqueous flowable composition comprising by % weight:

(a) 15%–20% fenazaquin, (b) 0.5%–2% sulfated alkyl carboxylate and sulfonated alkyl napthalene sodium salt, (c) 6%–12% sodium napthalene formaldehyde condensate, (d) 0–0.5% defoamer, (e) 0.02%–0.08% 1,2-benzisothiazolin-3-one, (f) 0.6%–1.0% one or more suspending agents, (g) 4%–8% propylene glycol, and (h) 50%–80% water.

5. A method of inhibiting a mite which comprises applying to a locus of the mite a composition of claim 1.

6. A method of inhibiting a mite which comprises applying to a locus of the mite a composition of claim 4.

* * * * *